United States Patent [19]

Campbell et al.

[11] 4,370,328

[45] Jan. 25, 1983

[54] CARDIAC STIMULANT 1-(3- OR 4-SUBSTITUTED PIPERIDINO)PHTHALAZINES

[75] Inventors: Simon F. Campbell, Kingsdown; John C. Danilewicz, Ash, Nr. Canterbury; Allan L. Ham, Broadstairs; John K. Stubbs, Deal, all of England

[73] Assignee: Pfizer Inc., New York, N.Y.

[21] Appl. No.: 170,777

[22] Filed: Jul. 21, 1980

Related U.S. Application Data

[63] Continuation-in-part of Ser. No. 34,653, Apr. 30, 1979, abandoned, which is a continuation-in-part of Ser. No. 953,557, Oct. 23, 1978, abandoned.

[30] Foreign Application Priority Data

Nov. 3, 1977 [GB] United Kingdom ............ 45670/77
Mar. 28, 1979 [GB] United Kingdom ............ 7910843

[51] Int. Cl.³ ........................................ C07D 237/30
[52] U.S. Cl. ........................... 424/250; 544/237
[58] Field of Search ..................... 544/237; 424/250

[56] References Cited

U.S. PATENT DOCUMENTS 4,001,422  1/1977  Danilewicz et al. ............ 424/251
4,289,772  9/1981  Campbell et al. ............... 424/250

FOREIGN PATENT DOCUMENTS 2021195 11/1970 Fed. Rep. of Germany .
1133406 11/1968 United Kingdom .
1199768  7/1970 United Kingdom .
1303061  1/1973 United Kingdom .

Primary Examiner—Nicholas S. Rizzo
Attorney, Agent, or Firm—Connolly and Hutz

[57] ABSTRACT

1-(3- or 4-substituted piperidino)phthalazines of the formula

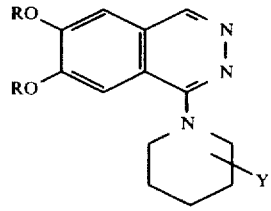

wherein R is $C_{1-6}$ alkyl; Y is a 3- or 4-position substituent and is $-X-(CHR^1)_m-Z$ wherein $R^1$ is hydrogen or $C_{1-6}$ alkyl; m is 1 or 2; X is oxygen or a direct link provided that when m is 1, X is a direct link; and Z is $-N(R^2)COR^3$, $-N(R^2)COOR^3$, $-N(R^2)SO_2R^3$, $-N(R^2)SO_2NR^4R^5$, $-N(R^2)SOR^3$, $-N(R^2)CONR^4R^5$ or $-OCONR^4R^5$, wherein $R^2$ and $R^5$ are each independently hydrogen or $C_{1-6}$ alkyl; $R^3$ is $C_{1-6}$ alkyl, phenethyl, benzyl, $C_{3-7}$ cycloalkyl, phenyl or pyridyl; $R^4$ is hydrogen or $R^3$; provided that when X is a direct link, $R^3$ or $R^4$ is $C_{3-7}$ cycloalkyl; the pharmaceutically acceptable acid addition salts thereof; processes for their preparation; and their use as cardiac stimulants and phosphodiesterase inhibitors.

14 Claims, No Drawings

CARDIAC STIMULANT 1-(3- OR 4-SUBSTITUTED PIPERIDINO)PHTHALAZINES

CROSS-REFERENCE TO RELATED APPLICATION

This application is a continuation-in-part of application Ser. No. 34,653, filed Apr. 30, 1979 and now abandoned which, in turn, is a continuation-in-part of application Ser. No. 953,557, filed Oct. 23, 1978 are now abandoned.

BACKGROUND OF THE INVENTION

1. Field of the Invention

This invention relates to novel derivatives of phthalazine and, more particularly, to 1-(3- or 4-substituted piperidino)phthalazines useful as cardiac stimulants and as phosphodiesterase inhibitors.

2. Description of the Prior Art

Quinazolines, reported to be cardiac stimulants, are claimed in U.S. Pat. No. 4,001,422.

German Offenlegungsschrift No. 2021195 discloses as anti-inflammatory, particularly antirheumatic agents, and as immunosuppressants, a series of 1-(substituted amino)- or 1-heterocyclicphthalazine derivatives. None of the compounds are reported to be cardiac stimulants.

British Pat. No. 1,133,406 describes a group of 1-(substituted amino)-4-(hydroxy- or alkoxyamino)-phthalazines and 1-heterocyclyl-4-(hydroxy- or alkoxyamino)phthalazines which are useful as antipyretic, antiinflammatory, hypotensive, bronchodilator and respiratory stimulant agents.

British Pat. No. 1,303,061 discloses as antiinflammatory agents, and in some cases as immunosuppressants, 1-aryl-1-aralkyl-4-aminophthalazines.

British Pat. No. 1,199,768 discloses a limited number of 4-aminoquinazoline derivatives as antihypertensive agents.

Copending application Ser. No. 908,664, filed May 23, 1978 and now abandoned, describes related 6,7-dimethoxy-1-(4-substituted piperidino)phthalazines useful as cardiac stimulants. Said compounds have the formula I wherein R is methyl and Y is a 4-position substituent and is defined as $-X-(CHR^1)_m-Z$ wherein X is a direct link, m is 0 and Z is as defined above, with the exception that Z never contains a cycloalkyl group.

SUMMARY OF THE INVENTION

The compounds of the invention are phosphodiesterase inhibitors and cardiac stimulants. The compounds are useful in the curative or prophylactic treatment of cardiac conditions, in particular heart failure.

According to the invention there is provided novel phthalazine compounds of the formula:

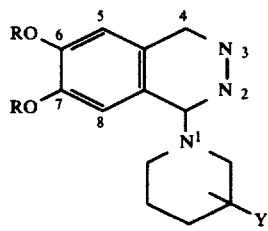

(I)

wherein R is a lower alkyl group; and

Y is attached to the 3- or 4-position of the piperidino ring and represents a group of the formula:

wherein $R^1$ is a hydrogen atom or a $C_{1-6}$ alkyl group, and $m_1$ is 1 or 2, with the proviso that when m is 2, each $R^1$ may be the same or different;

X is an oxygen atom or a direct link, with the proviso that when m is 1, X is a direct link; and Z is a group selected from:

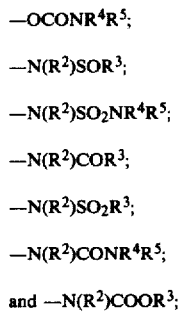

wherein $R^2$ and $R^5$ are each independently hydrogen or $C_{1-6}$ alkyl; $R^3$ is $C_{1-6}$ alkyl, $C_{3-7}$ cycloalkyl, phenethyl, benzyl, phenyl or 2-, 3- or 4-pyridyl; and $R^4$ is hydrogen or a group as defined for $R^3$ above; provided that when X is a direct link, $R^3$ or $R^4$ is $C_{3-7}$ cycloalkyl; and the pharmaceutically acceptable acid addition salts thereof.

The term $C_{1-6}$ applied to an alkyl or alkoxy group indicates that such a group contains up to 6 carbon atoms, preferably up to 4 carbon atoms, and such groups may be straight or, when appropriate, branched chain. The preferred cycloalkyl groups have 3 to 6 carbon atoms.

The compounds of the invention containing one or more asymmetric centers will exist as one or more pairs of enantiomers, and such pairs or individual isomers can be separated by physical methods, e.g. by fractional crystallization of suitable salts. The invention includes the separated pairs as well as mixtures thereof, i.e. racemic mixtures or as separated d- and l- optically-active isomeric forms.

The pharmaceutically acceptable acid addition salts of the compounds of the invention are those formed from acids which form non-toxic acid addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate, saccharate and p-toluenesulphonate salts.

The cardiac stimulant activity of the compounds of the invention is shown by their effectiveness in one or more of the following tests: (a) increasing the force of contraction in the isolated, spontaneously beating, guinea pig double atria preparation; (b) increasing myocardial contractility (left ventricular dP/dt max.) in the anesthetized dog with a left ventricular catheter; (c) increasing myocardial contractility in the conscious dog with an implanted left ventricular transducer.

In test (a) the positive inotropic and chronotropic responses of the atria to the test compound are measured at several doses and compared with the responses elicited by isoprenaline. The comparison of the dose response curves obtained gives a measure of the force versus rate selectivity of the test compound.

In test (b) the positive inotropic action of the test compound following intravenous administration is measured in the anesthetized dog. The magnitude and duration of this action, and the selectivity for increase in force versus frequency of contraction of the test compound are obtained, as are its peripheral effects, e.g. the effect on the blood pressure.

In test (c) the positive inotropic action of the test compound following intravenous or oral administration to a conscious dog with an implanted left ventricular transducer is measured. The magnitude of the inotropic action, the selectivity for increase in force versus frequency of contraction, and the duration of action of the inotropic effect of the test compound are all obtained.

The favored compounds of the invention have the formula:

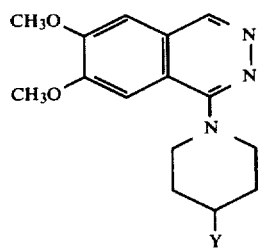 (II)

wherein Y is as defined for formula (I). The preferred compounds are those of formula (II) wherein X is a direct link;

"—$(CHR^1)_m$—" is preferably —$CH_2$—, —$CH(CH_3)$—, —$CH_2CH_2$—, or —$CH(CH_3)CH_2$—.

Z is preferably:

(a) $OCONR^4R^5$ wherein $R^4$ is $C_{3-6}$ cycloalkyl; and $R^5$ is hydrogen or $C_{1-4}$ alkyl;

(b) —$N(R^2)COR^3$ wherein $R^2$ is hydrogen or $C_1$-$C_4$ alkyl and $R^3$ is $C_{3-6}$ cycloalkyl;

(c) —$N(R^2)SO_2R^3$ wherein $R^2$ is hydrogen or $C_1$-$C_4$ alkyl and $R^3$ is $C_{3-6}$ cycloalkyl;

(d) —$N(R^2)CONR^4R^5$ wherein $R^2$ is hydrogen or $C_1$-$C_4$ alkyl, $R^5$ is hydrogen or $C_1$-$C_4$ alkyl, and $R^4$ is $C_{3-6}$ cycloalkyl;

(e) —$N(R^2)COOR^3$ wherein $R^2$ is hydrogen or $C_1$-$C_4$ alkyl, and $R^3$ is $C_{3-6}$ cycloalkyl.

The preferred individual compounds have the formula (II) wherein Y is:

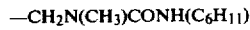

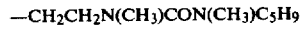

The invention also includes the pharmaceutically acceptable bioprecursors of the compounds of the formula (I).

The term "pharmaceutically acceptable bioprecursor" requires some explanation. It is, of course, common practice in pharmaceutical chemistry to overcome some undesirable physical or chemical property of a drug by converting the drug into a chemical derivative which does not suffer from that undesirable property, but which, upon administration to an animal or human being, is converted back to the parent drug. For example, if a drug is not well absorbed when given to the animal or patient, by the oral route, it may be possible to convert it into a chemical derivative which is well absorbed and which in the serum or tissues is reconverted to the parent drug. Again, if a drug is unstable in solution, it may be possible to prepare a chemical derivative of it which is stable and may be administered in solution, but which is reconverted in the body to give the parent drug. The pharmaceutical chemist is well aware of the possibility of overcoming intrinsic deficiencies in a drug by chemical modifications which are only temporary and are reversible upon administration to the animal or patient.

For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

The compounds of the invention can be administered alone but will generally be administered in admixture with a pharmaceutical carrier selected with regard to the intended route of administration and standard pharmaceutical practice. For example they can be administered orally in the form of tablets containing such excipients as starch or lactose, or in capsules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which can contain other solutes, for example, enough salts or glucose to make the solution isotonic.

For administration to man in the curative or prophylactic treatment of cardiac conditions such as congestive heart failure, oral dosages of the most active compounds of the invention will be in the range from 20 mg. to 1 g. daily, taken in 2 to 4 divided doses per day, for an average adult patient (70 kg.). Dosages for intravenous administration are within the range 1 to 300 mg. per single dose as required, for example in the treatment of acute heart failure. Thus for a typical adult patient, individual tablets or capsules will contain from 5 to 250 mg. of active compound, in a suitable pharmaceutically acceptable vehicle or carrier.

Thus the present invention provides a pharmaceutical composition comprising a compound of the formula (I) as defined above or pharmaceutically acceptable acid addition salt thereof together with a pharmaceutically acceptable diluent or carrier.

The invention also provides a method of stimulating the heart of an animal, including a human being, which comprises administering to the animal a compound of the formula (I) or salt thereof as defined above, or a pharmaceutical composition as defined above, in an amount sufficient to stimulate the heart of the animal.

The compounds of the invention are prepared by a number of routes:

Route A

Compounds of the formula (I) are prepared by reacting an appropriately substituted phthalazine of the formula:

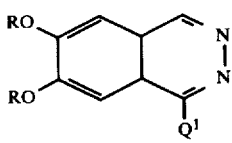

wherein $Q^1$ represents a facile leaving group such as chloro-, bromo-, iodo-, lower alkoxy or (lower alkyl)thio, with an amine of the formula:

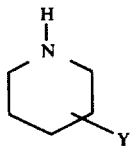

with resultant elimination of $HQ^1$. $Q^1$ is preferably chloro or bromo. The reaction is preferably carried out in an inert organic solvent such as ethanol with heating, e.g. under reflux, in a temperature range of 75° C. to 150° C. for up to about 72 hours. When $Q^1$ is chloro-, bromo- or iodo-, the presence of a base such as triethylamine or of excess reagent of the formula (IV) is advantageous. The product is isolated and purified by conventional methods.

The compounds of the formulae III and IV are either known compounds or are prepared by procedures analogous to the prior art, e.g. by the hydrogenation of the corresponding pyridine derivatives.

Route B

Compounds of the formula (I) in which Z is $-N(R^2)CONHR^4$ are prepared by the reaction of a phthalazine of the formula:

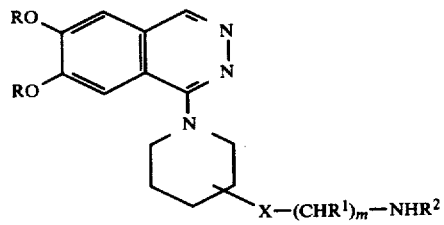

with an isocyanate $R^4NCO$, $R^4$ being other than hydrogen, or, to prepare compounds in which $R^4$ is H, sodium or potassium cyanate in the presence of acid. The acid can be supplied by using an acid addition salt of the compound of the formula (V) as the starting material.

In a typical procedure, the reactants are reacted together at room temperature for up to 24 hours in a suitable solvent, e.g. dry chloroform. The mixture is then evaporated to leave an oil which is triturated with e.g. a mixture of ether and ethyl acetate to leave the product as a crystalline solid which can be recrystallized from a suitable solvent, e.g. ethanol.

Route C

Compounds of the formula (I) wherein Z is either $-N(R^2)COR^3$, $-N(R^2)COOR^3$, $-N(R^2)SO_2R^3$, or $-N(R^2)CONR^4R^5$, $R^4$ and $R^5$ both being other than hydrogen in the latter case, can be prepared by reacting a compound of the formula (V) as previously defined with, as appropriate, either: (a) a haloformate of the formula $Q^2COOR^3$ or acyl halide of the formula $R^3COQ^2$, wherein $Q^2$ is chloro or bromo; (b) a sulfonyl halide of the formula $R^3SO_2Q^2$, $Q^2$ being chloro or bromo; (c) a carbamyl halide of the formula $R^4R^5NCOQ^2$ wherein $R^4$ and $R^5$ are both other than hydrogen and $Q^2$ is chloro or bromo; or (d) an anhydride of the formula $(R^3CO)_2O$.

Typically the reactants are allowed to stand together at room temperature for a period of up to 24 hours in an inert organic solvent, e.g. chloroform, in the presence of a base such as triethylamine, or n-butyllithium in tetrahydrofuran.

The product is isolated and purified by conventional methods, e.g. by washing with aqueous base, drying and evaporating the organic layer to leave an oil, dissolving the oil in ethyl acetate and applying it to a column of e.g. "Florisil" (Trade Mark), the product being eluted with e.g. 10% ether in ethyl acetate.

Route D

Compounds of the formula (I) wherein Z is $-OCONHR^4$ are prepared by reacting a phthalazine of the formula:

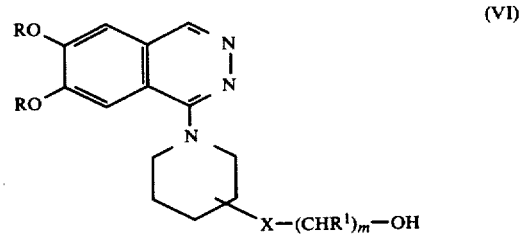

with an isocyanate $R^4NCO$, $R^4$ being other than hydrogen, or, to prepare compounds in which $R^4$ is hydrogen, sodium or potassium cyanate in the presence of acid.

In a typical procedure, the reactants are heated together in a suitable organic solvent, e.g. dry chloroform, at 40°–70° C. for 5–10 hours. The solution is then evaporated in vacuo to leave an oil which is triturated with e.g. ether to leave a residue which can be chromatographed on a suitable column to purify it.

Route E

Compounds of the formula (I) in which Z is $-N(R^2)COR^3$, are prepared by reacting a phthalazine of the formula (V) as previously defined with an ester of N-hydroxy succinimide of the formula:

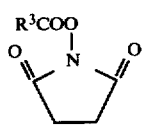

The corresponding ester of N-hydroxyphthalimide can also be used.

In a typical procedure, the reactants are stirred together in a suitable solvent, e.g. by dry chloroform, for 2–6 hours at room temperature.

The product is isolated and purified by conventional methods.

The starting esters are prepared by conventional techniques, typically by reaction of an acid of the formula $R^3COOH$ with H-hydroxysuccinimide or N- hydroxyphthalimide in the presence of dicyclohexylcarbodiimide.

Acid addition salts of the compounds of formula (I) are prepared from the crude or pure free base product by the conventional technique of reacting the free base with the acid in an inert solvent, e.g. by mixing alcoholic solutions of each and collecting the resulting precipitate by filtration. The product is then recrystallized to purity.

The phthalazine starting materials used in the preceding routes can be prepared by procedures analogous to those of the prior art. Similarly, the piperidine and other starting materials used are either known compounds or are prepared by conventional methods. The preparation of many starting materials is illustrated in Preparations 1 to 17.

The following Examples illustrate the invention:

EXAMPLE 1

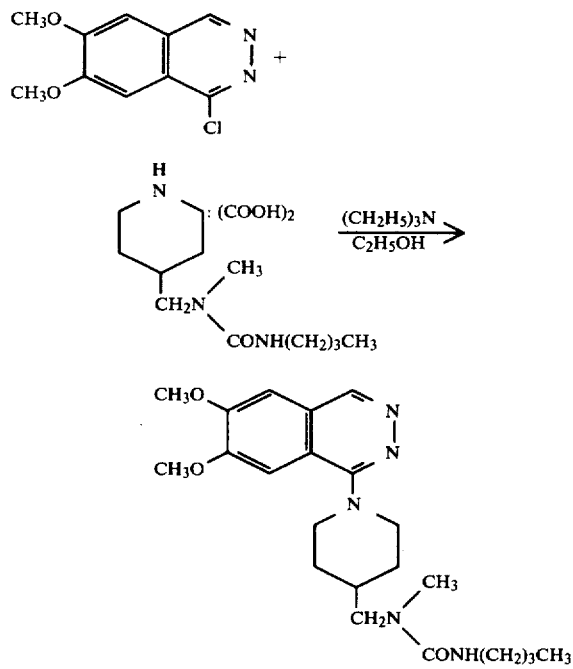

1-Chloro-6,7-dimethoxyphthalazine (1.12 g.), 4-[(1-methyl-3-n-butylureido)methyl]piperidine mono-oxalate (2.0 g.) and triethylamine (2.5 ml.) were heated together under reflux for 100 hours in ethanol (100 ml.).

After concentration in vacuo, the residue was suspended in water (25 ml.), basified to pH 10 with 5 N sodium hydroxide solution and extracted into chloroform (2×25 ml.). The dried (MgSO$_4$) extracts were taken to dryness in vacuo giving a brown oil which was dissolved in the minimum volume of chloroform and applied to the top of a chloroform "Florisil" (Trademark) column (bed size 30×2.5 cm.) which was eluted with chloroform containing increasing quantities of methanol (up to 50%). After 500 ml. of solvent had been collected 18×60 ml. fractions were taken of which fractions 12–18 were combined and taken to dryness in vacuo. The resultant oil, which solidified on cooling, was dissolved in the minimum volume of ethyl acetate and left in a refrigerator for 18 hours to crystallize. Crystals of pure 6,7-dimethoxy-1-[4-([1-methyl-3-n-butylureido]methyl)piperidino]phthalazine monohydrate (0.37 g.) were collected by filtration, softening at 100° C., and melting at 114°–127° C.

Analysis %: Found: C, 60.6; H, 8.1; N, 15.9. Calculated for C$_{22}$H$_{33}$N$_5$O$_3$.H$_2$O: C, 61.0; H, 8.1; N, 16.2.

EXAMPLES 2–32

The following compounds were prepared similarly to Example 1, starting from 1-chloro-6,7-dimethoxyphthalazine and the appropriately substituted piperidine.

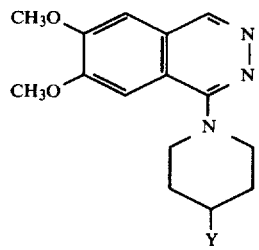

| Example No. | Y | Form Isolated and m.p. (°C.) | Analysis % (Theoretical in brackets) | | |
|---|---|---|---|---|---|
| | | | C | H | N |
| 2 | —CH$_2$CH$_2$NHCOOC$_2$H$_5$ | Oxalate, 177° | 55.5 | 6.4 | 11.8 |
| | | | (55.2 | 6.3 | 11.7) |
| 3 | —CH$_2$N(CH$_3$)COCH$_3$ | Oxalate, 180° | 56.6 | 6.3 | 12.1 |
| | | | (56.2 | 6.3 | 12.5) |
| 4 | —CH$_2$CH$_2$N(CH$_3$)COCH$_3$ | Hydrochloride monohydrate, 112° | 55.7 | 6.9 | 13.1 |
| | | | (56.3 | 7.3 | 13.1) |
| 5 | —CH$_2$NHCOCH$_3$ | Free base, 226°–228° | 62.8 | 7.0 | 16.3 |
| | | | (62.8 | 7.0 | 16.3) |
| 6 | —CH$_2$N(CH$_3$)SO$_2$CH$_3$ | Free base, 192°–193° | 54.8 | 6.6 | 14.0 |
| | | | (54.8 | 6.7 | 14.2) |
| 7 | —CH$_2$CH$_2$N(CH$_3$)SO$_2$CH$_3$ | Hydrochloride hemihydrate, 200° | 50.2 | 6.8 | 12.7 |
| | | | (50.3 | 6.7 | 12.3) |
| 8 | —CH$_2$N(CH$_3$)CONH(CH$_2$)$_2$CH$_3$ | Free base, 188°–189° | 62.8 | 7.9 | 17.4 |
| | | | (62.8 | 7.8 | 17.4) |
| 9 | —CH$_2$CH$_2$NHCONHC$_2$H$_5$ | Free base, 180° | 61.6 | 7.6 | 17.8 |
| | | | (62.0 | 7.5 | 18.1) |
| 10 | —CH$_2$CH$_2$N(CH$_3$)CONHCH$_2$CH$_3$ | Free base, 186°–187° | 62.8 | 8.1 | 17.6 |
| | | | (62.8 | 7.8 | 17.4) |
| 11 | —CH$_2$N(CH$_3$)COOCH$_2$CH$_3$ | Hydrochloride, | 56.0 | 6.9 | 13.1 |

-continued

| Example No. | Y | Form Isolated and m.p. (°C.) | Analysis % (Theoretical in brackets) C | H | N |
|---|---|---|---|---|---|
|  |  | 181°–182° | (56.5 | 6.9 | 13.2) |
| 12 | —CH$_2$N(CH$_3$)CONHCH$_3$ | Free base, 217°–218° | 61.1 (61.1 | 7.4 7.3 | 18.7 18.8) |
| 13 | —CH$_2$CH$_2$NHSO$_2$.Phenyl | Solvate with one mole of CHCl$_3$, 206°–208° | 50.2 (50.1 | 5.1 5.1 | 9.7 9.7) |
|  |  |  | (Also, Cl$^\ominus$: Found: 18.7, Calculated 18.5) | | |
| 14 | —CH$_2$N(CH$_3$)CO(CH$_2$)$_2$CH$_3$ | Free base, 144°–145° | 65.5 (65.3 | 7.9 7.8 | 14.5 14.5) |
| 15 | —CH$_2$CH$_2$N(CH$_3$)COOC$_2$H$_5$ | Hydrochloride, 170°–171° | 57.6 (57.5 | 7.4 7.1 | 12.0 12.8) |
| 16 | —(CH$_2$CH$_2$N(CH$_3$)SO$_2$.Phenyl | Hydrochloride hemihydrate, 203°–204° | 56.0 (55.9 | 6.0 6.3 | 10.8 10.9) |
| 17 | —CH$_2$N(CH$_3$)CO.Phenyl | Hemihydrate, 158°–160° | 67.4 (67.1 | 6.9 6.8 | 13.2 13.0) |
| 18 | —CH$_2$CH$_2$N(CH[CH$_3$]$_2$)SO$_2$CH$_3$ | Oxalate, 153°–154° | 52.1 (52.5 | 6.4 6.5 | 10.4 10.6) |
| 19 | —CH(CH$_3$)CH$_2$N(CH$_3$)SO$_2$CH$_3$ | Free base, 168°–169° | 57.0 (56.9 | 7.2 7.2 | 13.0 13.3) |
| 20 | —CH$_2$CH$_2$N(CH$_3$)SO$_2$(CH$_2$)$_2$CH$_3$ | Hydrochloride hemihydrate, 166°–168° | 52.6 (52.3 | 7.2 7.1 | 11.3 11.6) |
| 21 | —CH$_2$CH$_2$N(CH$_3$)SO$_2$.Benzyl | Oxalate monohydrate, 188°–190° | 54.7 (54.7 | 6.4 6.1 | 9.7 9.5) |
| 22 | —CH(CH$_3$)CH$_2$N(CH$_3$)COCH$_3$ | Oxalate dihydrate, 97°–110° | 53.2 (53.9 | 6.2 7.1 | 10.6 10.9) |
| 23 | —CH$_2$CH$_2$NHSO$_2$CH$_3$ | Free base, 181°–182° | 55.4 (54.8 | 6.6 6.6 | 14.0 14.2) |
| 24 | —CH$_2$N(CH$_3$)SO$_2$.Phenyl | Hydrochloride monohydrate, 210°–212° | 53.6 (54.1 | 5.7 6.1 | 11.3 11.0) |
| 25 | —CH$_2$N(CH$_3$)CON(CH$_3$)$_2$ | Oxalate sesquihydrate, 83°–87° | 52.6 (52.4 | 6.4 6.8 | 14.0 13.9) |
| 26 | —CH$_2$CH$_2$N(CH$_3$)SO$_2$C$_2$H$_5$ | Hydrochloride monohydrate, 192°–194° | 50.4 (50.4 | 6.6 7.0 | 12.1 11.7) |
| 27 | —CH$_2$CH$_2$NHCOCH$_3$ | Free base, 183° | 63.8 (63.7 | 7.4 7.3 | 16.1 15.6) |
| 28 | —CH(CH$_3$)N(CH$_3$)COCH$_3$ | 1¼ oxalate, ½ hydrate, 105°–108° | 53.6 (53.5 | 6.0 6.2 | 11.1 10.8) |
| 29 | —CH(CH$_3$)CH$_2$N(CH$_3$)SO$_2$C$_2$H$_5$ | Free base, 148°–150° | 57.5 (57.8 | 7.4 7.4 | 12.9 12.8) |
| 30 | —CH(CH$_3$)N(CH$_3$)CONHC$_2$H$_5$ | Oxalate, 1¼ hydrate, 135°–137° | 53.4 (53.3 | 7.0 7.0 | 14.1 13.5) |
| 31 | —OCH$_2$CH$_2$N(CH$_3$)COCH$_3$ | 1¼ oxalate, 127°–143° | 53.1 (52.8 | 6.2 6.0 | 10.6 10.7) |
| 32 | —OCH$_2$CH$_2$N(CH$_3$)SO$_2$CH$_3$ | Oxalate, 154°–160° | 49.2 (49.0 | 5.9 5.9 | 10.5 10.9) |

Example 33

Preparation of 6,7-Dimethoxy-1-[4-(2-[3-(3-pyridyl)-1-methylureido]ethyl) piperidino]phthalazine

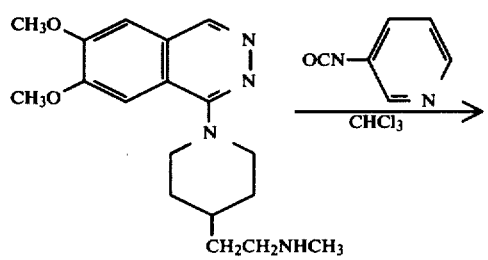

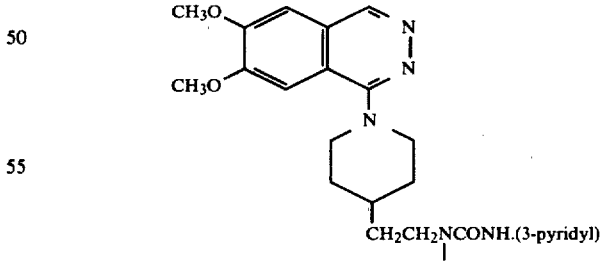

6,7-Dimethoxy-1-[4-(2-N-methylaminoethyl)-piperidino]-phthalazine (1 g.) in dry chloroform (10 ml.) was stirred and heated with 3-pyridyl isocyanate (0.6 g.). After allowing the mixture to stand overnight the mixture was washed with water, dried (Na$_2$CO$_3$) and evaporated to dryness in vacuo to give an oil. The oil was triturated with a mixture of ether and ethyl acetate (30 ml., 9:1) to produce a crystalline solid which was recrystallized from ethanol to give pure 6,7-dimethoxy-1-[4-(2-[3-(3-pyridyl)-1-methylureido]ethyl)-piperidino]phthalazine ¼ hydrate (0.45 g.), m.p. 200°–204° C.

Analysis %: Found: C, 63.2; H, 6.7; N, 18.1. $C_{24}H_{30}N_6O_3 \cdot \frac{1}{4}H_2O$ requires: C, 63.3; H, 6.8; N, 18.5.

EXAMPLES 34 TO 36

The following compounds were prepared similarly to the previous Example, starting from 6,7-dimethoxy-1-[4-(2-N-methylaminoethyl or N-methylaminomethyl)-piperidino]-phthalazine and the appropriate isocyanate.

6,7-Dimethoxy-1-[4-(2-N-methylaminoethyl)-piperidino]-phthalazine (0.7 g.) in a mixture of dry chloroform (25 ml.) and triethylamine (2 ml.), was stirred while N,N-dimethyl-carbamoyl chloride (0.23 g.) was added slowly, dropwise. The mixture was then allowed to stand overnight after which water (20 ml.) was added. The chloroform layer was separated, dried ($Na_2CO_3$) and evaporated to dryness in vacuo. The oily residue was retaken in the minimum quantity of ethyl acetate and was then applied to the top of a column of "Florisil" (Trademark) (bed size 35 cm. × 1.5 cm.) Elution was commenced with 10% ether in ethyl acetate and ten fractions, each of 50 ml., were collected. Frac-

| Example No. | Y | Form Isolated and m.p. (°C.) | Analysis % (Theoretical in brackets) | | |
|---|---|---|---|---|---|
| | | | C | H | N |
| 34 | —CH$_2$CH$_2$N(CH$_3$)CONH(CH$_2$)$_2$CH$_3$ | 1¼ Oxalate hydrate, 88°–95° | 52.6 (52.8 | 6.7 6.7 | 12.0 12.3) |
| 35 | —CH$_2$CH$_2$N(CH$_3$)CONH.C$_6$H$_5$ | Oxalate dihydrate, 144°–146° | 56.3 (56.3 | 5.8 6.5 | 11.7 12.2) |
| 36 | —CH$_2$N(CH$_3$)CONH.(3-pyridyl) | Free base, 250°–252° | 62.9 (63.3 | 6.5 6.5 | 19.2 19.3) |

EXAMPLE 37

Preparation of 6,7-Dimethoxy-1-[4-(2-[1,3,3-trimethylureido]ethyl)-piperidino]phthalazine

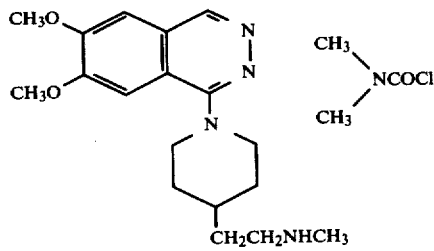

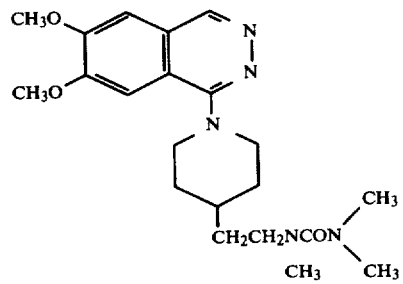

tions 3 to 9 were combined and evaporated to dryness in vacuo to give an oil which solidified on trituration with ether containing 10% ethyl acetate. Recrystallization from ethyl acetate gave pure 6,7-dimethoxy-1-[4-(2-[1,3,3-trimethylureido]ethyl)piperidino]phthalazine (0.2 g.), m.p. 140°–141° C.

Analysis %: Found: C, 62.6; H, 7.8; N, 17.2. $C_{21}H_{31}N_5O_3$ requires: C, 62.8; H, 7.8; N, 17.4.

EXAMPLES 38 TO 41

The following Examples were prepared similarly to the previous Example, starting from 6,7-dimethoxy-1-[4-(2-N-methylaminoethyl or N-methylaminoethyl)-piperidino]phthalazine and the appropriate sulfonyl chloride, acid chloride or carbamoyl chloride.

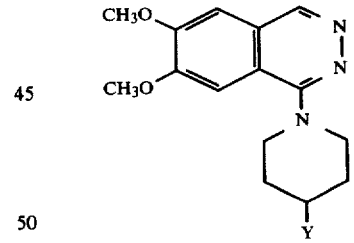

| Example No. | Y | Form Isolated and m.p. (°C.) | Analysis % (Theoretical in brackets) | | |
|---|---|---|---|---|---|
| | | | C | H | N |
| 38 | —CH$_2$CH$_2$N(CH$_3$)SO$_2$.(3-pyridyl) | Dihydrochloride ¼ hydrate, softens at 110° and decomposes at 155° | 50.0 (49.9 | 5.8 5.6 | 12.5 12.6) |
| 39 | —CH$_2$N(CH$_3$)COCH$_2$CH$_2$.Phenyl | Free base, 144°–145° | 69.3 (69.6 | 7.3 7.2 | 12.2 12.5) |
| 40 | —CH$_2$N(CH$_3$)SO$_2$.(3-pyridyl) | 1¼ Oxalate ¼ hydrate, 100°–112° | 50.4 (49.9 | 5.3 5.2 | 11.7 11.6) |

-continued

| Example No. | Y | Form Isolated and m.p. (°C.) | Analysis % (Theoretical in brackets) | | |
|---|---|---|---|---|---|
| | | | C | H | N |
| 41 | —CH₂CH₂N(CH₃)CON<br>        \<br>        CH₃ | Phenyl | Oxalate ½ hydrate, 164°–166° | 59.7 (59.8 | 6.4 6.5 | 12.0 12.5) |

EXAMPLE 42

Preparation of 6,7-Dimethoxy-1-[3-(N-ethylcarbamoyloxymethyl)-piperidino]phthalazine

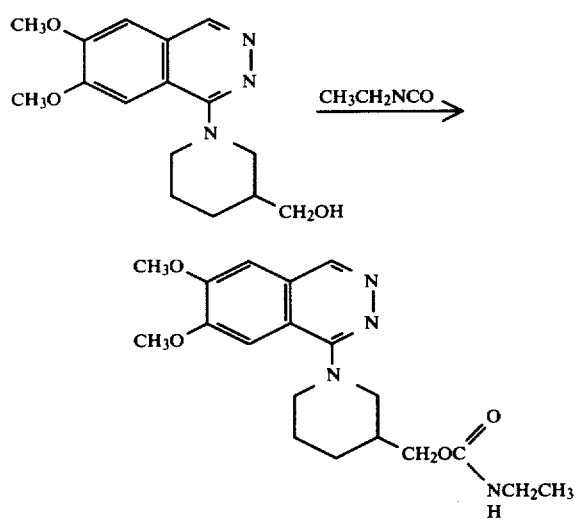

Ethyl isocyanate (0.69 g.) was added slowly to the stirred solution of 6,7-dimethoxy-1-[3-(hydroxymethyl)-piperidino]phthalazine (0.76 g.) in dry chloroform (10 ml.) at 5° C., then heated at 60° C. for 7 hours. Thin layer chromatography showed that the reaction had not gone to completion so more ethyl isocyanate (0.5 ml.) was added and stirring was continued at room temperature for 18 hours. The solution was then concentrated in vacuo to give an oil which was triturated with ether (30 ml.) and decanted. The residue was dissolved in the minimum volume of chloroform and applied to the top of a chromatography column, made up of chloroform and powdered silica (bed size 40×2 cm.), which was then eluted with chloroform containing increasing quantities of methanol (up to 5%). 100 ml. Fractions were collected and monitored by thin layer chromatography. Appropriate fractions were combined and concentrated in vacuo to give the product as an oil (0.45 g.).

This oil was suspended in ethyl acetate (25 ml.) and enough ethanol was added to give a complete solution, then a solution of oxalic acid in ethyl acetate was added until the mixture was acidic (pH 3–4). The precipitate was collected by filtration and crystallized from iso-propyl alcohol to yield 6,7-dimethoxy-1-[3-(N-ethylcarbamoyloxymethyl)piperidino]phthalazine: mono-oxalate:½ hydrate (0.30 g.), m.p. 132°–134° C.

Analysis %: Found: C, 53.4; H, 5.9; N, 11.9. Calculated for $C_{19}H_{26}N_4O_4:C_2H_2O_4:\frac{1}{2}H_2O$: C, 53.8; N, 6.1; N, 11.9.

EXAMPLES 43 TO 46

The following compounds were prepared similarly to the previous Example, starting from 6,7-dimethoxy-1-[4-(2-hydroxyethyl or 2-hydroxyethoxy)piperidino]phthalazine and the appropriate isocyanate.

| Example No. | Y | Form Isolated and m.p. (°C.) | Analysis % (Theoretical in brackets) | | |
|---|---|---|---|---|---|
| | | | C | H | N |
| 43 | —CH₂CH₂OCONHC₂H₅ | Free base, 159°–160° | 61.4 (61.8 | 7.1 7.3 | 14.6 14.4) |
| 44 | —OCH₂CH₂OCONHC₂H₅ | Oxalate, 163°–169° | 53.1 (53.4 | 6.1 6.1 | 11.7 11.3) |
| 45 | —CH₂CH₂OCONH.Phenyl | Free base, 197°–199° | 65.6 (66.0 | 6.6 6.5 | 13.1 12.8) |
| 46 | —CH₂CH₂OCONH(3-pyridyl) | Dioxalate, hydrate 162°–165° | 51.2 (51.0 | 5.0 5.2 | 11.3 11.0) |

EXAMPLE 47

Preparation of 6,7-Dimethoxy-1-[4-(2-N-nicotinoyl-N-methylamino]ethyl) piperidino]phthalazine To a stirred suspension of nicotinic acid (2.3 g.) in dry chloroform (350 ml.) at 30° C., were added N-hydroxysuccinimide (2.3 g.) and N,N-dicyclohexylcarbodiimide (4.1 g.). After five minutes the suspension had substantially dissolved and was then gradually replaced by a white crystalline precipitate. The mixture was stirred for a further 1 hour and was then filtered. An aliquot of the filtrate (60 ml.) was treated with a solution of 6,7-dimethoxy-1-[4-(2-N-methylaminoethyl)-piperidino]phthalazine (1 g.) in dry chloroform (20 ml.) and the solution was stirred at ambient temperature for 2.5 hours, after which water (50 ml.) was added. The chloroform layer was separated, washed with water (20 ml.), dried (MgSO₄) and evaporated in vacuo to give an oil containing a small amount of solid. The oil-solid mixture was stirred with chloroform (15 ml.), filtered and the filtrate was evaporated in vacuo to give an oil. The oil was dissolved in iso-propanol (30 ml.), treated with an iso-propanol solution of oxalic acid (to pH 2) and the precipitated solid was recovered by filtration. Recrystallization from iso-propanol gave pure 6,7-dimethoxy-1-[4-(2-[N-nicotinoyl-N-methylamino]ethyl)-piperidino]phthalazine oxalate monohydrate (290 mg.), m.p. 110°–115° C.

Analysis %: Found: C, 56.9; H, 5.8; N, 12.7. $C_{24}H_{29}N_5O_3 \cdot C_2H_2O_4 \cdot H_2O$ requires: C, 57.4; H, 6.1; N, 12.9.

EXAMPLE 48 thalazine and the appropriate piperidine, and were isolated in the form indicated:

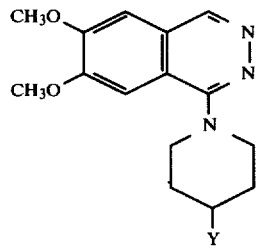

| Example No. | Y | Form Isolated and m.p. ([C.]) | Analysis % (Theoretical in brackets) | | |
|---|---|---|---|---|---|
| | | | C | H | N |
| 49 | —$CH_2N(CH_3)CONH.cyclohexyl$ | Hydrochloride hydrate, 210–212° | 58.2 (58.1 | 7.1 7.7 | 14.4 14.1) |
| 50 | —$CH_2CH_2N(CH_3)CON(CH_3)cyclopentyl$ | Oxalate hemihydrate, 178–179° | 58.6 (58.5 | 7.2 7.3 | 12.1 12.6) |
| 51 | —$CH_2N(CH_3)SO_2.cyclopentyl$ | Oxalate hemihydrate, 203–204° | 52.4 (52.6 | 6.5 6.4 | 10.4 10.2) |
| 52 | —$CH_2CH_2N(CH_3)SO_2.cyclohexyl$ | Oxalate, 209–210° | 54.9 (55.1 | 6.2 6.8 | 9.4 9.9) |

Preparation of 6,7-dimethoxy-1-[4-(1,3-dimethyl-3-cyclohexylureidomethyl)piperidino]phthalazine oxalate 1-Chloro-6,7-dimethoxyphthalazine (1.0 g.), 1,3-dimethyl-1-(4-piperidylmethyl)-3-cyclohexylurea (2.8 g.), ethanol (25 ml.) and triethylamine (5 ml.) were heated under reflux for 48 hours. The mixture was then concentrated in vacuo to give a black residue which was dissolved in chloroform (30 ml.), washed with water (2×25 ml.) dried and concentrated in vacuo. The resultant oil was dissolved in the minimum volume of ethyl acetate and applied to the top of a "Florisil" (Trade Mark)/ethyl acetate column (bed size 16 cm.×1.5 cm.). The column was eluted with ethyl acetate/5% ether (100 ml.) then neat ethyl acetate. 12×30 ml. Fractions were collected by thin layer chromatography, were combined and concentrated in vacuo.

The oxalate salt was precipitated by the addition of excess oxalic acid in isopropanol to a solution of the crude product in the same solvent.

Recrystallization from isopropanol gave 6,7-dimethoxy-1-[4-(1,3-dimethyl-3-cyclohexylureidomethyl)-piperidino]phthalazine oxalate hemihydrate (150 mg.), m.p. 195°–197° C.

Analysis %: Found: C, 58.6; H, 7.3; N, 12.3. $C_{25}H_{27}N_5O_3.C_2H_2O_4\frac{1}{2}H_2O$ requires: C, 58.5; H, 7.3; N, 12.6.

EXAMPLES 49 TO 52

The following compounds were prepared similarly to Example 48, starting from 1-chloro-6,7-dimethoxyph-thalazine and the appropriate piperidine, and were isolated in the form indicated:

EXAMPLE 53

Preparation of 6,7-dimethoxy-1-[4-[2-(3-cyclohexyl-1-methylureido)ethyl]piperidino]phthalazine Cyclohexyl isocyanate (0.5 g.) in dry chloroform (5 ml.) was added dropwise to 6,7-dimethoxy-1-[4-[2-(methylamino)ethyl]piperidino]phthalazine (1.0 g.) in dry chloroform (10 ml.) with stirring and ice-water cooling. After further stirring at room temperature (20°) for 1 hour the mixture was concentrated in vacuo, triturated with minimum quantity of ethyl acetate and filtered. The resultant solid was dissolved in methylene chloride (10 ml.), filtered, treated with ethyl acetate (20 ml.) and gently distilled to remove methylene chloride. The residual ethyl acetate solution was left standing in the refrigerator overnight to precipitate crystalline 6,7-dimethoxy-1-[4-[2-(3-cyclohexyl-1-methylureido)ethyl]piperidino]phthalazine (820 mg.), m.p. 204°–206° C.

Analysis %: Found: C, 65.6; H, 8.2; N, 15.2. $C_{25}H_{37}N_5O_3$ requires: C, 65.9; H, 8.2; N, 15.4.

EXAMPLES 54 AND 55

The following compounds were prepared similarly to Example 53, starting from 6,7-dimethoxy-1-[4-2-(methylamino)-ethyl piperidino]phthalazine or 6,7-dimethoxy-1-[4-(methylamino)methyl)piperidino]phthalazine and cyclopentyl isocyanate.

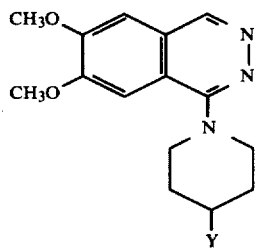

| Example No. | Y | Form Isolated and m.p. (°C.) | Analysis % (Theoretical in brackets) | | |
|---|---|---|---|---|---|
| | | | C | H | N |
| 54 | —CH$_2$CH$_2$N(CH$_3$)CONH.cyclopentyl | Hemihydrate, 198–199° | 64.0 (64.0 | 8.1 8.1 | 15.5 15.5) |
| 55 | —CH$_2$N(CH$_3$)CONH.cyclopentyl | Free base, 204–205° | 64.6 (64.6 | 7.8 7.8 | 16.4 16.4) |

EXAMPLE 56

Preparation of 6,7-dimethoxy-1-[4-(2-[4-cyclohexylcarbonyl-N-methylamino]ethyl)piperidino phthalazine oxalate Cyclohexyl carbonyl chloride (0.5 ml.) in dry chloroform (5 ml.) was added dropwise to a solution of 6,7-dimethoxy-1-[4-[2-(methylamino)ethyl]piperidino]-phthalazine (0.5 g.) and triethylamine (1 ml.) in dry chloroform (10 ml.) with stirring and ice-water cooling. After further stirring at room temperature (20°) for 2 hours the mixture was shaken with water (20 ml.) and the chloroform phase dried (Na$_2$CO$_3$) and concentrated in vacuo. The resultant oil was dissolved in the minimum volume of ethyl acetate and applied to the top of a "Florisil" (Trade Mark)/ethyl acetate colum (bed size 12×1.5 cm.) followed by elution with ethyl acetate/10% ether. Ten 30 ml. fractions were collected and appropriate fractions (identified by thin-layer chromatography) were combined and concentrated in vacuo. The residual oil was dissolved in the minimum quantity of isopropanol and converted to the oxalate salt by the addition of an isopropanol solution of oxalic acid to pH 4.0.

Recrystallization of the precipitated solid from isopropanol gave 6,7-dimethoxy-1-[4-(2-[4-cyclohexylcarbonyl-N-methyl-amino]ethyl)piperidino]phthalazine oxalate hemihydrate (150 mg.), m.p. 187°–8° C.

Analysis %: Found: C, 60.2; H, 7.2; N, 9.9. C$_{25}$H$_{36}$N$_4$O$_3$.C$_2$H$_2$O$_4$.½H$_2$O requires: C, 60.1; H, 7.3; N, 10.4.

EXAMPLES 57–60

The following compounds were prepared similarly to Example 56, starting from 6,7-dimethoxy-1-[4-[2-(methylamino)ethyl]piperidino]phthalazine or 6,7-dimethoxy-1-[4-(methylaminomethyl)piperidino]phthalazine and the appropriate acid chloride.

| Example No. | Y | Form Isolated and m.p. (°C.) | Analysis % (Theoretical in brackets) | | |
|---|---|---|---|---|---|
| | | | C | H | N |
| 57 | —CH$_2$CH$_2$N(CH$_3$)CO.cyclopentyl | Oxalate 1½ hydrate, 153–155° | 57.0 (57.4 | 6.7 7.2 | 10.2 10.3) |
| 58 | —CH$_2$CH$_2$N(CH$_3$)CO.cyclobutyl | Oxalate hemihydrate 168–171° | 58.1 (58.7 | 6.6 6.9 | 11.2 11.0) |
| 59 | —CH$_2$N(CH$_3$)CO.cyclopentyl | Dioxalate, 125–126° | 54.6 (54.7 | 6.3 6.1 | 9.2 9.5) |
| 60* | —CH$_2$N(CH$_3$).CO.cyclopropyl | Hemihydrate 195–197° | 64.2 (64.1 | 7.4 7.4 | 14.1 14.2) |

EXAMPLE 61

The following compounds are prepared from appropriate reactants according to the procedure of Example 43.

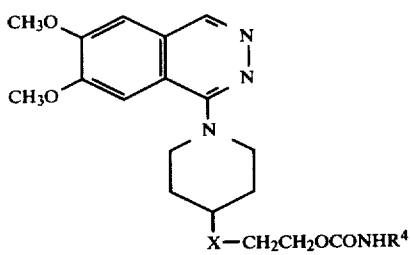

| X | R⁴ | X | R⁴ |
|---|---|---|---|
| direct link | cyclopropyl | O | cyclopropyl |
| direct link | cyclopentyl | O | cyclobutyl |
| direct link | cyclohexyl | O | cyclohexyl |
| direct link | cycloheptyl | O | cycloheptyl |
| direct link | CH₂CH₂phenyl | O | CH₂CH₂phenyl |
| direct link | n-C₆H₁₃ | O | n-C₆H₁₃ |
| direct link | n-C₄H₉ | O | n-C₄H₉ |
| direct link | CH₂phenyl | O | CH₂phenyl |
|  |  | O | 4-pyridyl |

EXAMPLE 62

The compounds tabulated below are prepared from the appropriate piperidines and 1-chloro-6,7-dimethoxyphthalazine according to the procedure of Example 1.

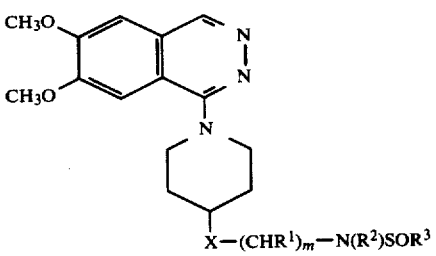

| X | R¹ | m | R² | R³ |
|---|---|---|---|---|
| — | H | 2 | H | CH₃ |
| — | H | 2 | CH₃ | n-C₆H₁₃ |
| — | CH₃ | 1 | H | 4-pyridyl |
| — | H | 2 | H | C₆H₅ |
| O | H | 2 | H | C₂H₅ |
| O | H | 2 | H | C₆H₁₁ |
| — | H | 2 | CH₃ | C₅H₉ |
| — | H | 1 | CH₃ | CH₂CH₂C₆H₅ |

The following Preparations illustrate the preparation of certain of the starting materials:

PREPARATION 1

Preparation of 4-(2-Acetamidoethyl)piperidine

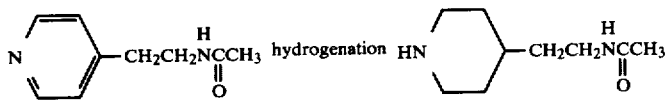

4-(2-Acetamidoethyl)pyridine (33 g.) in ethanol (250 ml.) was acidified to pH 4 with hydrochloric acid and hydrogenated at 60 p.s.i./60° C. over a platinum oxide catalyst for 18 hours, after which time the uptake of hydrogen was complete. The catalyst was then removed by filtration and the filtrate was treated with a solution of potassium hydroxide flakes in methanol (1.1 molar equivalents) and refiltered. The solvents were distilled off in vacuo, leaving a clear oil, which on standing gave 4-(2-acetamidoethyl)piperidine (18 g.) as a white solid, m.p. 60° C.

The oxalate salt was also prepared, m.p. 125°-129° C.

Analysis %: Found: C, 50.9; H, 7.7; N, 10.4. Calculated for C₉H₁₈N₂O:C₂H₂O₄: C, 50.8; H, 7.8; N, 10.8.

PREPARATION 2

(A) 4-(3-n-Butyl-1-methylureidomethyl)pyridine 4-(N-Methylaminomethyl)pyridine (3.6 g.) in dry chloroform (70 ml.) was stirred and cooled in an ice bath while n-butyl-isocyanate (9.9 g.) was added slowly, dropwise. The mixture was then allowed to stand at ambient temperature overnight after which methanol (15 ml.) was added and stirring continued for a further 30 minutes. The solvents were removed by evaporation to dryness in vacuo and the residue was redissolved in ethyl acetate (50 ml.). The oxalate salt was precipitated by treating the solution with a slight excess of oxalic acid in ethyl acetate. Recrystallization from isopropanol gave pure 4-(3-n-butyl-1-methylureidomethyl)pyridine sesqui-oxalate (7.2 g.), m.p. 86°-90° C.

Analysis %: Found: C, 50.4; H, 6.6; N, 11.9. C₁₂H₁₉N₃O.1 1/2 (C₂H₂O₄) requires: C, 50.6; H, 6.2; N, 11.8.

Also synthesized by a similar method were:
4-(1,3-Dimethylureidomethyl)pyridine (crude base, unpurified)
4-(2-[3-Ethylureido]ethyl)pyridine (crude base, unpurified)
4-(1-Methyl-3-n-propylureidomethyl)pyridine (crude base, unpurified)
4-(2-[3-Ethyl-1-methylureido]ethyl)pyridine (crude base, unpurified) and
dl-4-(1-[3-ethyl-1-methylureido]ethyl)pyridine (crude base, unpurified).

(B) The above pyridines were then hydrogenated to the corresponding piperidines similarly to Preparation 1.

PREPARATION 3

(A) Preparation of 4-(2-methanesulphonamidoethyl)pyridine

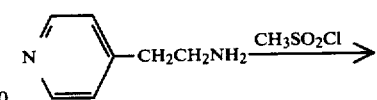

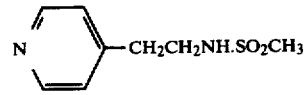

Methanesulphonyl chloride (3.5 g.) was added slowly to 4-(2-aminoethyl)pyridine (3.6 g.) and triethylamine (3.0 g.) in chloroform (40 ml.). The temperature was maintained below 40° C. during the addition, after which the orange solution was left to stand at room temperature overnight. Water (50 ml.) was then added, the chloroform phase was separated, and the aqueous phase extracted with chloroform (100 ml.). The two chloroform solutions were combined, dried (MgSO$_4$) and taken to dryness in vacuo to give a yellow oil which solidified immediately. This solid was crystallized from ethanol to yield white crystals of 4-(2-methanesulphonamidoethyl)pyridine (1.4 g.).

A small sample was recrystallized from ethanol, m.p. 114°–116° C.

Analysis %: Found: C, 47.9; H, 6.0; N, 14.0. Calculated for C$_8$H$_{12}$N$_2$O$_2$S: C, 48.0; H, 6.0; N, 14.0.

(B) Preparation of 4-(2-methanesulphonamidoethyl)-piperidine

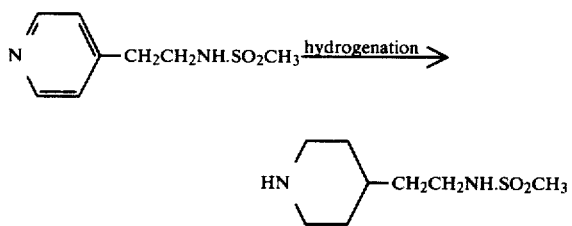

4-(2-methanesulphonamidoethyl)pyridine (8.4 g.) in ethanol (85 ml.) was acidified to pH 2 with 2 N HCl and hydrogenated at room temperature and a pressure of 50 p.s.i. over a platinum oxide catalyst until hydrogen uptake ceased. The catalyst was then removed by filtration and the filtrate was taken to dryness in vacuo to give a white solid which was dissolved in the minimum volume of hot ethanol, filtered quickly, and left at room temperature overnight. The resultant white crystals were collected by filtration and dried to yield 4-(2-methanesulphonamidoethyl)piperidine hydrochloride (8.3 g.), m.p. 165°–167° C.

Analysis %: Found: C, 39.6; H, 7.8; N, 11.7. Calculated for C$_8$H$_{18}$N$_2$O$_2$S.HCl: C, 39.6; H, 7.9; N, 11.5.

Also synthesized in a similar fashion to Part (A) were:
4-(2-[N-isopropyl-methanesulphonamido]ethyl)-pyridine oxalate, m.p. 129°–131° C.; Found: C, 46.7; H, 6.2; N, 8.0; C$_{11}$H$_{18}$N$_2$O$_2$S.C$_2$H$_2$O$_4$ requires: C, 47.0; H, 6.1; N, 8.4%.
4-(2-[N-methyl-methanesulphonamido]ethyl)pyridine (crude oil).
4-(2-[N-methyl-benzenesulphonamido]ethyl)pyridine (crude oil).
4-(2-benzenesulphonamidoethyl)pyridine, m.p. 109°–110° C.; Found: C, 59.5; H, 5.4; N, 10.6; C$_{13}$H$_{14}$N$_2$O$_2$S requires: C, 59.5; H, 5.4; N, 10.7%.
dl-4-(3-[N-methyl-methanesulphonamido]prop-2-yl)pyridine oxalate, m.p. 155°–158° C.
4-(2-[N-methyl-n-propanesulphonamido]ethyl)-pyridine (crude oil).
4-(2-[N-methyl-phenylmethanesulphonamido]-ethyl)-pyridine, m.p. 109°–110° C.; Found: C, 62.0; H, 6.3; N, 9.7; C$_{15}$H$_{18}$N$_2$O$_2$S requires: C, 62.1; H, 6.3; N, 9.7%.
4-(N-methyl-methanesulphonamidomethyl)pyridine (crude).
4-(2-[N-methyl-ethanesulphonamido]ethyl)pyridine (crude oil).
dl-4-(1-[N-methyl-ethanesulphonamido]prop-2-yl)-pyridine hydrochloride (crude oil) and
4-(N-methyl-benzenesulphonamidomethyl)pyridine, m.p. 101°–102° C.; Found: C, 59.9; H, 5.4; N, 11.1; C$_{13}$H$_{14}$N$_2$O$_2$S requires: C, 59.5; H, 5.4; N, 10.7%.

The above were then hydrogenated similarly to Part (B) to give the corresponding piperidines.

PREPARATION 4

(A) 4-(N-Methyl-butyramidomethyl)pyridine n-Butyryl chloride (2.8 ml.) in dry methylene chloride (20 ml.) was added slowly to a stirred, cooled mixture of 4-(N-methylaminomethyl)pyridine (3 g.) and triethylamine (5 ml.) in dry methylene chloride (30 ml.). The mixture was then stirred at room temperature for 2.5 hours, after which water (30 ml.) was added. The organic phase was separated, washed with dilute aqueous sodium hydroxide (5%, 30 ml.), dried (Na$_2$CO$_3$) and evaporated to dryness in vacuo. The resultant dark brown oil (3.8 g.) was chromatographed on a "Florisil" (Trademark) (15 g.) column, using chloroform as eluant. Appropriate fractions were identified by TLC, bulked and evaporated in vacuo to give pure 4-(N-methylbutyramidomethyl)pyridine as an oil (3.2 g.).

(B) The oil was then hydrogenated similarly to Preparation 1(B) to the corresponding piperidine.

Also prepared similarly to the above were:
4-[N-methyl-benzamidomethyl]pyridine, and 4-[1,3,3-trimethylureidomethyl]pyridine (crude oil), which were then hydrogenated as Preparation 1(B) to the corresponding piperidines.

PREPARATION 5

4-(1-[N-Methylacetamido]prop-2-yl)pyridine 4-(1-N-Methylamino-prop-2-yl)pyridine (4.5 g.) in acetic acid (15 ml.) was treated cautiously with acetic anhydride (10 ml.) followed by allowing the mixture to stand at ambient temperature overnight. Methanol (20 ml.) was then added to destroy excess acetic anhydride, followed by evaporation in vacuo (at 40° C.) to remove methanol and methyl acetate. The residue was diluted with water and treated portionwise with said sodium carbonate (anhydrous) until alkaline (pH 10–12). The oily suspension was extracted with chloroform (3×60 ml.) and the bulked extracts were dried (Na$_2$CO$_3$) and evaporated to dryness in vacuo to give a near-colorless oil (6.8 g.). The oil was distilled to give pure dl-4-(1-[N-methylacetamido]prop-2-yl)pyridine (3 g.), b.p. 138°–140° C./0.4 m.m. Hg. (as a colorless oil).

Analysis %: Found: C, 65.8; H, 8.5; N, 14.2. C$_{11}$H$_{16}$N$_2$O.1/2 H$_2$O requires: C, 65.7; H, 8.5; N, 13.9%.

The following compounds were synthesized by a similar method:
4-(2-[N-methylacetamido]ethyl)pyridine oxalate, m.p. 120°–124° C.,
4-(2-Acetamidoethyl)pyridine, b.p. 158°–160° C./0.6 m.m.,
4-(Acetamidomethyl)pyridine, m.p. 83°–88° C.,
4-(N-methylacetamidomethyl)pyridine (crude oil), and
dl-4-(1-[N-methylacetamido]ethyl)pyridine (crude oil).

The above were then hydrogenated similarly to Preparation 1 to give the corresponding piperidines.

PREPARATION 6

4-(2-[N-Ethoxycarbonyl-N-methylamino]-ethyl)pyridine

Ethyl chloroformate (11.2 g.) was added dropwise to a cooled, stirred mixture of 4-(2-N-methylaminoethyl)-pyridine (13.6 g.) and triethylamine (25 g.) in dry chloroform (400 ml.). The mixture was stirred at room temperature overnight and then water (100 ml.) was added. The organic layer was separated, dried (MgSO$_4$) and evaporated in vacuo to give 4-(2-[N-ethoxycarbonyl-N-methylamino]ethyl)pyridine as an oil (20 g.).

Also prepared similarly to the above was: 4-(2-[N-ethoxycarbonylamino]ethyl)pyridine.

The above products were then hydrogenated similarly to Preparation 1 to produce the corresponding piperidines.

PREPARATION 7

Preparation of 6,7-dimethoxy-1-(3-hydroxymethylpiperidino)phthalazine

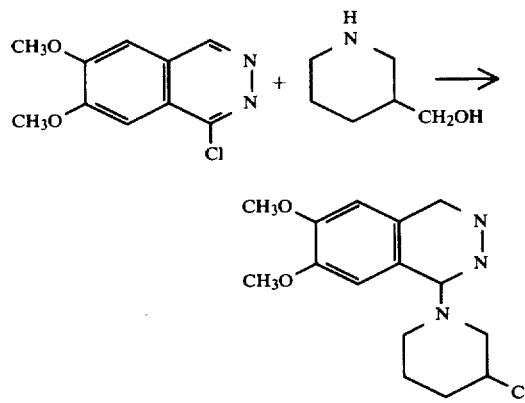

1-Chloro-6,7-dimethoxy phthalazine (2.25 g.), 3-hydroxymethylpiperidine (1.72 g.) and triethylamine (1.3 ml.) in iso-amyl alcohol (60 ml.) were heated at 95° C. for 42 hours. The cooled reaction mixture was then filtered and the filtrate was taken to dryness in vacuo. The residue was dissolved in water (100 ml.), 5 N sodium hydroxide solution was added to give a pH of 11 and the basic mixture was then extracted with chloroform (2×100 ml.). The chloroform extracts were combined, dried (MgSO$_4$) and concentrated in vacuo to give a brown oil, which was triturated with ether (50 ml.) and filtered. The resultant solid was crystallized twice from acetonitrile, yielding 6,7-dimethoxy-1-(3-hydroxymethylpiperidino)phthalazine (1.83 g.), m.p. 162°–165° C.

Analysis %: Found: C, 63.7; H, 6.9; N, 13.7. Calculated for C$_{16}$H$_{21}$N$_3$O$_3$: C, 63.4; H, 7.0; N, 13.9.

Also synthesized by a similar route were (a) 6,7-dimethoxy-1-[4-(2-hydroxyethyl)piperidino]phthalazine, m.p. 168°–171°.

Analysis %: Found: C, 64.0; H, 7.4; N, 13.7. Calculated for C$_{17}$H$_{22}$N$_3$O$_3$: C, 64.3; H, 7.3; N, 13.2; and (b) 6,7-dimethyl-1-[4-(2-hydroxyethoxy)piperidino]-phthalazine, m.p. 171°–173°

Analysis %: Found: C, 16.2; H, 6.8; N, 12.7. Calculated for C$_{17}$H$_{22}$N$_3$O$_4$: C, 61.2; H, 7.0: N, 12.6.

PREPARATION 8

4-(2-isopropylaminoethyl)pyridine

4-Vinylpyridine (21 g), iso-propylamine (24 g) concentrated hydrochloric acid (40 g) and water (100 ml) were mixed together with cooling, and then boiled under reflux for 20 hours. The mixture was cooled, basified to pH 12-13 (20% NaOH) and extracted with chloroform (3×200 ml). The bulked extracts were washed with water (100 ml) dried (MgSO$_4$) and evaporated in vacuo to give a green oil. The oil was distilled and the fraction boiling at 84°–90° C./1 mm. was collected (16.5 g) and identified (by NMR spectroscopy) as 4-(2-iso-propylaminoethyl)pyridine. Also synthezied by a similar route were:
4-(2-aminoethyl)pyridine,
4-(2-methylaminoethyl)pyridine, and
dl-[(1-methylamino)prop-2-yl]pyridine.

PREPARATION 9

6,7-Dimethoxy-1-[4-(2-N-methylaminoethyl)-piperidino]phthalazine 6,7-Dimethoxy-1-[4-(2-N-methylacetamidoethyl)-piperidino]phthalazine (2.0 g.) (prepared as in Example 4) in a mixture of ethanol and 5 N sodium hydroxide solution (1:1, 20 ml.) was heated under reflux for 70 hours. The ethanol was removed by evaporation in vacuo and the aqueous phase was diluted with water (10 ml.) and extracted with chloroform. The extract was dried (Na$_2$CO$_3$) and evaporated in vacuo to give an oil, which on trituration with hexane gave 6,7-dimethoxy-1-[4-(2-N-methylaminoethyl)piperidino]phthalazine as a pale yellow solid (1.5 g.). A small sample was characterized as the dioxalate monohydrate, m.p. 159°–162° C.

Analysis %: Found: C, 49.8; H, 5.7; N, 10.3. Calculated for C$_{18}$H$_{26}$N$_4$O$_2$.2C$_2$H$_2$O$_4$.H$_2$O: C, 50.0; H, 6.1; N, 10.6.

6,7-Dimethoxy-1-[4-(N-methylaminomethyl)-piperidino]-phthalazine was prepared similarly to the above, starting with 6,7-dimethoxy-1-[4-(N-methylacetamidomethyl)piperidino]phthalazine (prepared as in Example 3). A small sample of the product was characterized as the dioxalate, softening at 140° C., with decomposition at 180° C.

Analysis %: Found: C, 50.1; H, 5.7; N, 11.5 Calculated for C$_{17}$H$_{24}$N$_4$O$_2$.2C$_2$H$_2$O$_4$: C, 50.8; H, 5.7; N, 11.3.

PREPARATION 10

A. Preparation of 6,7-Dimethoxyphthalazine-1-one

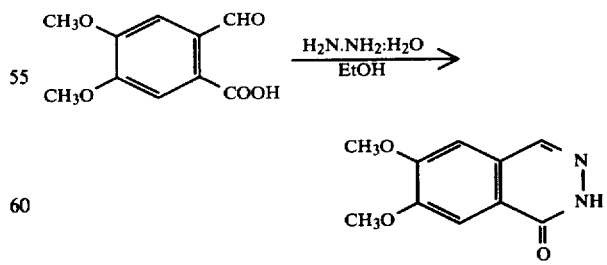

4,5-Dimethoxyphthalaldehydic acid (10 g.) and hydrazine hydrate (2.4 ml.) in ethanol (150 ml.) were heated under reflux for 20 hours during which time a white crystalline solid formed. The mixture was cooled in an ice bath, filtered and the resulting product dried to give crude 6,7-dimethoxyphthalazin-1-one (7 g.). A sample was crystallized from water yielding colorless needles, m.p. 254°–256° C.

Analysis %: Found: C, 58.4; H, 4.8; N, 13.9. Calculated for $C_{10}H_{10}N_2O_3$: C, 58.3; H, 4.9; N, 13.6.

B. Preparation of 1-Chloro-6,7-dimethoxyphthalazine

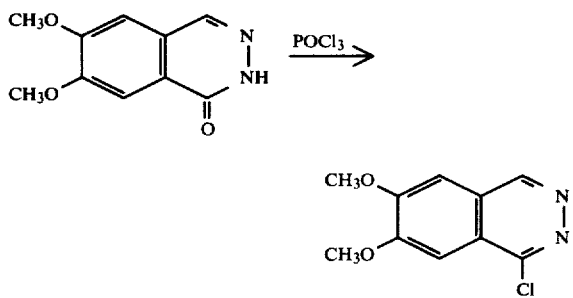

6,7-Dimethoxyphthalazin-1-one (20.6 g.) was heated under reflux with phosphoryl chloride (200 ml.) for 6 hours then cooled to room temperature and the excess phosphoryl chloride removed under reduced pressure. The resultant brown solid was suspended in acetone (150 ml.) and poured onto cold (5° C.) concentrated ammonium hydroxide (200 ml.). The crude product was filtered, washed with water (200 ml.) then petroleum ether (200 ml.). The pale yellow solid was dried (20 g.), dissolved in the minimum volume of chloroform and precipitated with excess petroleum ether, after which it was recovered by filtration, washed again with petroleum ether (100 ml.) and dried to give 1-chloro-6,7-dimethoxyphthalazine (13 g.), m.p. 195°–197° C. with decomposition.

Analysis %: Found: C, 53.3; H, 4.2; N, 12.7. Calculated for $C_{10}H_9ClN_2O_2$: C, 53.5; H, 4.0; N, 12.5.

PREPARATION 11

(A) Preparation of 1-Benzyl-4-(2,2-diethoxyethoxy)-piperidine

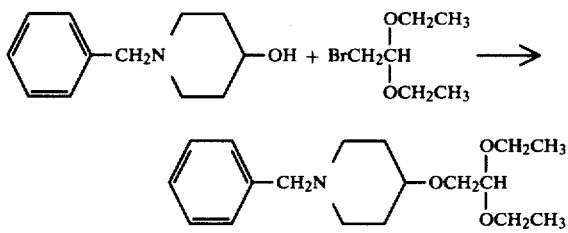

1-Benzyl-4-hydroxy piperidine (11.5 g.) dissolved in dry dimethylformamide (DMF) (25 ml.) was added dropwise to a stirred suspension of sodium hydride (2.8 g. of 50% dispersion in oil in dry DMF [25 ml.]), under dry nitrogen, and then stirred at room temperature for 3 hours. The suspension was cooled in an ice/water bath while 2-bromoacetaldehyde diethylacetal (13.0 g.) in dry dimethylformamide (25 ml.) was added dropwise, followed by stirring at room temperature for 24 hours. The above process was repeated to add more sodium hydride (2.8 g.) and the acetal (13.0 g.). Iso-propyl alcohol (50 ml.) was added, and the mixture was stirred for ½ hour, followed by filtration through "Hyflo" (Trademark). The filtrate was concentrated in vacuo, suspended in water (100 ml.) and basified to pH 11 with 5 N sodium hydroxide. After extraction with chloroform (2×100 ml.) the combined extracts were taken to dryness in vacuo to give an orange oil which was distilled in vacuo to give 1-benzyl-4-(2,2-diethoxyethoxy)-piperidine (14.1 g.), b.p. 152° C.@0.1 mm.

(B) Preparation of 1-benzyl-4-[2-(N-methylacetamido)-ethoxy]piperidine

1-Benzyl-4-(2,2-diethoxyethoxy)piperidine (50 g.) and 2 N hydrochloric acid (130 ml.) were stirred together at room temperature for 18 hours. The mixture was basified to pH 9 with 5 N sodium hydroxide, extracted into chloroform (2×150 ml.), dried (MgSO₄) and taken to dryness in vacuo. The oil was dissolved in ethanol (150 ml.) and mixed with sodium acetate trihydrate (8.9 g.), water (83 ml.), glacial acetic acid (28 ml.) and 33% w/w ethanolic methylamine solution (15.5 g.). The stirred solution was cooled to 0° C. in an ice/salt bath and the temperature was maintained at 0°±2° C. while sodium borohydride (6.6 g.) was added portionwise and then for the following ½ hour. The mixture was stirred at room temperature for 40 hours, adjusted to pH 7 with a little 5 N sodium hydroxide, concentrated in vacuo, diluted with water (150 ml.) and extracted with ether (2×225 ml.). The aqueous phase was basified to pH 10 with 5 N sodium hydroxide, extracted into chloroform (2×180 ml.), dried (MgSO₄) and taken to dryness in vacuo.

The crude oil (12.5 g.) in dry chloroform (80 ml.) and triethylamine (10.4 ml.) was stirred and cooled in an ice/water bath during the slow addition of acetic anhydride (6.1 g.). The mixture was stirred at room temperature for 2 hours, shaken with water (50 ml.) and separated. The chloroform phase was dried (MgSO₄), taken to dryness in vacuo, leaving a brown gum which was dissolved in ethyl acetate and converted to the oxalate salt by addition of oxalic acid in ethyl acetate solution to pH 3. The ethyl acetate was removed by decantation and the residual gum was dissolved in hot iso-propyl alcohol, allowed to cool to room temperature and diluted with an equal volume of ether to deposit a brown gum. The gum was isolated by decantation of the solvents and dried to give crude 1-benzyl-4-[2-(N-methylacetamido)-ethoxy]piperidine oxalate (10 g.).

A second crop of the same material was obtained from the iso-propyl alcohol/ether solution. Recrystallization of this from methyl cyanide gave pure crystals of 1-benzyl-4-[2-(N-methylacetamido)ethoxy]piperidine: mono-oxalate:monohydrate, m.p. 142°–147° C.

Analysis %: Found: C, 57.1; H, 7.0; N, 6.8. Calculated for $C_{17}H_{26}N_2O_2 \cdot C_2H_2O_4 \cdot H_2O$: C, 57.3; H, 7.6; N, 7.0.

The product was hydrogenated as previously described to remove the benzyl group.

PREPARATION 12

4-[2-(N-methylsulfonamido)ethoxy]piperidine was prepared similarly to the above, but using methane-sulfonyl chloride in place of acetic anhydride in step (B).

PREPARATION 13

Preparation of 1-Methyl-1-(4-pyridyl-methyl)-3-phenylurea 4-(Methylaminomethyl)pyridine (5 g), dry chloroform (500 ml) and phenyl isocyanate (5 g) were stirred together at room temperature for 2 hours. The chloroform was then evaporated in vacuo and the resultant oil was redissolved in the minimum quantity of chloroform and chromatographed on a "Florisil" (Trade Mark) (100 g) column using chloroform containing gradually increasing quantities of methanol (up to 2.5%) as eluting solvent. Appropriate fractions (identified by t.l.c.) were combined and evaporated in vacuo to give 1-methyl-1-(4-pyridylmethyl)-3-phenylurea as an oil (8.0 g).

N.m.r. and mass spectroscopic data were compatible with the required structure:

| Mass spec.: | M+ 241. |
|---|---|
| n.m.r. (CDCl$_3$) | δ8.5 (doublet) Pyridyl ring protons |
| | δ7.3 (doublet) |
| | δ7.12 (multiplet) Phenyl ring protons |
| | δ4.6 (singlet) Methylene protons |
| | δ3.0 (singlet) N—methyl protons |

PREPARATION 14

Preparation of 1,3-Dimethyl-1-(4-pyridylmethyl)-3-phenylurea

Phosgene in toluene (50 ml, 12½% solution was stirred at 0°–10° whilst a mixture of N-methylaniline (5.4 g) and triethylamine (15 ml) in dry chloroform (100 ml) was added slowly dropwise. On completion of the addition the mixture was stirred for 19 hours at room temperature, then cooled to 0°–10° whilst a solution of 4-(N-methylaminomethyl)pyridine (3.1 g) in dry chloroform (70 ml) was slowly added. The mixture was stirred at room temperature overnight followed by the cautious addition of 2 N hydrochloric acid (20 ml). After 1 hour, 5 N sodium hydroxide (12 ml) was added and the organic phase was separated, washed (H$_2$O, 50 ml), dried (Na$_2$CO$_3$) and evaporated in vacuo to give a dark oil. The oil was dissolved in the minimum quantity of chloroform and chromatographed on a "Florisil" (Trademark) column eluted with chloroform. Appropriate fractions were identified by thin layer chromatography, combined and evaporated in vacuo to give 1,3-dimethyl-1-(4-pyridylmethyl)-3-phenylurea as a dark oil (3 g). The n.m.r. spectrum was compatible with the required structure.

Also made by a similar route was:

1,3-dimethyl-1-(2-[4-pyridyl]ethyl)-3-cyclopentylurea (crude oil):

| n.m.r. (CDCl$_3$): | δ8.49 (doublet) } pyridyl |
|---|---|
| | δ7.10 (doublet) } protons; |
| | singlets 2.55 and 2.78 (protons of methyl groups); |
| | triplets at δ ~ 3.4 } |
| | and δ ~ 3.0 } —CH$_2$—CH$_2$—protons |
| | δ1.4–δ1.8 (complex signal, cyclohexyl protons) |

PREPARATION 15

Preparation of N-methyl-N-(2-[4-pyridyl]-ethyl)cyclohexanesulphonamide

N-Methyl-2-(4-pyridyl)ethylamine (5 g) was added dropwise over 15 minutes to a stirred suspension of sodium hydride (1.77 g, 50% dispersion in oil) in dry N,N-dimethylformamide (80 ml) (DMF) containing absolute ethanol (2 drops) under dry nitrogen at room temperature. Upon gentle warming to 50° for 1 hour the coloured anion was generated. After cooling to 0°, cyclohexanesulphonyl chloride (6.71 g) was added dropwise over 45 minutes then the stirred mixture allowed to attain room temperature over 18 hours. The yellow solution was then added to ice-water (200 ml), filtered, extracted with chloroform (25 ml×4), the organic phase dried (MgSO$_4$) and concentrated in vacuo. Residual DMF was distilled from the product at 0.7 mm.Hg and the remaining viscous oil column-chromatographed upon silica (150 g) by elution with chloroform. Evaporation of the primary fractions (200 ml × 3) afforded crystalline N-methyl-N-(2-[4-pyridyl]ethyl)cyclohexanesulphonamide (8.67 g), m.p. 94°–6°.

| n.m.r. (CDCl$_3$) | δ8.5 (2H, double doublet) |
|---|---|
| | δ7.15 (2H, double doublet) |
| | δ3.45 (2H, complex signal) |
| | δ2.9 (6H, complex signal) |
| | δ2.2–1.0 (10H, envelope of many signals) |

Also prepared by a similar procedure, but using triethylamine in chloroform in place of sodium hydride in dimethylformamide, was N-methyl-N-(2-[4-pyridyl]ethyl)cyclopentanesulphonamide, 2.5 g (crude oil).

| n.m.r. (CDCl$_3$): | δ8.5 (2H, double doublet) |
|---|---|
| | δ7.2 (2H, double doublet) |
| | δ4.3 (2H, singlet) |
| | δ3.4 (1H, complex signal) |
| | δ2.8 (3H, singlet) |
| | δ2.3–1.0 (8H, envelope of many signals) |

PREPARATION 16

Preparation of 1-methyl-1-(4-piperidylmethyl)-3-cyclohexylurea

1-Methyl-1-(4-pyridylmethyl)-3-phenylurea (7.0 g) in glacial acetic acid (50 ml) was hydrogenated over platinum oxide at 60°/60 p.s.i. until uptake of hydrogen ceased. The catalyst was removed by filtration and the filtrate evaporated in vacuo. The resultant oil was basified with 5 N NaOH (to pH 12) and extracted with chloroform (2×50 ml). The combined extracts were dried (MgSO$_4$) and evaporated with chloroform (2×50 ml). The combined extracts were dried (MgSO$_4$) and evaporated to give 1-methyl-1-(4-piperidylmethyl)-3-cyclohexylurea as an oil (4.0 g). The n.m.r. and mass spectra were compatible with the required structure.

The following compounds were prepared in a similar manner from the pyridine derivatives:

(a) 1,3-Dimethyl-1-(4-piperidylmethyl)-3-cyclohexylurea (crude oil) (structure confirmed by n.m.r.).

(b) 1,3-Dimethyl-1-(4-piperidylmethyl)-3-cyclohexylurea (crude oil):

n.m.r. (CDCl$_3$): singlets at 2.68 and 2.80 p.p.m. (1,3-dimethyl protons) (on acetate salt form), complex signals at δ1.3–1.8 p.p.m. (shielded cyclic alkane protons) complex signals at δ2.5–2.9) (deshielded cyclic alkane) (3.0–3.5) and straight chain protons adjacent to nitrogens i.r.: C=O: 1625 cm$^{-1}$ (c) N-methyl-N-(4-piperidylmethyl)cyclopentanesulphonamide:

n.m.r. (CDCl$_3$): δ3.6–2.4 (11H, envelope of signals including those of the —NCH$_3$ protons at δ2.9—singlet) δ2.4–1.0 (13H, envelope of signals) and (d) N-methyl-N-(2-[4-piperidyl]ethyl)cyclohexanesulphonamide:

n.m.r. (CDCl$_3$): δ3.85 (1H, D$_2$O exchangeable) δ3.4–2.4 (10H, complex signal) δ2.4–0.9 (17H, envelope of many signals).

PREPARATION 17

The following compounds are prepared according to the procedure of Preparation 3 but using the appropriate amine and R$^3$SOCl reactants.

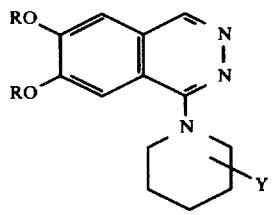

H—N⟨ ⟩—X—(CHR$^1$)$_m$—N(R$^2$)SOR$^3$

| X | R$^1$ | m | R$^2$ | R$^3$ |
|---|---|---|---|---|
| — | H | 2 | H | CH$_3$ |
| — | H | 2 | CH$_3$ | n-C$_4$H$_9$ |
| — | H | 2 | H | N—C$_6$H$_{13}$ |
| — | n-C$_4$H$_9$ | 2 | n-C$_4$H$_9$ | CH$_3$ |
| — | H | 2 | H | C$_6$H$_5$ |
| — | H | 2 | C$_2$H$_5$ | CH$_2$C$_6$H$_5$ |
| — | CH$_3$ | 1 | H | 4-pyridyl |
| — | H | 1 | H | C$_2$H$_5$ |
| — | H | 1 | CH$_3$ | CH$_2$CH$_2$C$_6$H$_5$ |
| O | H | 2 | H | C$_2$H$_5$ |
| O | CH$_3$ | 2 | CH$_3$ | C$_6$H$_5$ |
| O | C$_2$H$_5$ | 2 | C$_2$H$_5$ | C$_3$H$_5$ |
| O | H | 2 | H | C$_6$H$_{11}$ |
| — | H | 2 | CH$_3$ | C$_5$H$_9$ |

We claim:

1. A compound of the formula:

(I)

wherein

R is a C$_{1-6}$ alkyl group;

and Y is attached to the 3- or 4-position of the piperidino ring and represents a group of the formula:

—X—(CHR$^1$)$_m$—Z wherein

R$^1$ is selected from the group consisting of hydrogen and C$_{1-6}$ alkyl;

m is 1 or 2, with the proviso that when m is 2, each R$^1$ may be the same or different;

X is selected from the group consisting of oxygen and a direct link, with the proviso that when m is 1, X is a direct link; and Z is selected from the group consisting of —OCONR$^4$R$^5$, N(R$^2$)SO$_2$NR$^4$R$^5$, —N(R$^2$)COR$^3$, —N(R$^2$)SO$_2$R$^3$, —N(R$^2$)CONR$^4$R$^5$, N(R$^2$)SOR$^3$, and —N(R$^2$)COOR$^3$; wherein R$^2$ and R$^5$ are each independently selected from the group consisting of hydrogen and C$_{1-6}$ alkyl; R$^3$ is selected from the group consisting of C$_{1-6}$ alkyl, benzyl, C$_{3-7}$ cycloalkyl, phenyl, phenethyl and pyridyl; and R$^4$ is selected from the group consisting of hydrogen and R$^3$; provided that when X is a direct link, R$^3$ or R$^4$ is C$_{3-7}$ cycloalkyl;

and the pharmaceutically-acceptable acid addition salts thereof.

2. A compound according to claim 1 having the formula

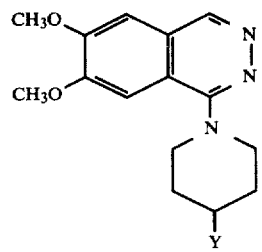

(II)

wherein Y is as defined in claim 1.

3. A compound according to claim 2 wherein X is a direct link, and —(CHR$^1$)$_m$— is selected from the group consisting of —CH$_2$—, —CH(CH$_3$)—, —CH$_2$CH$_2$—, and —CH(CH$_3$)CH$_2$—.

4. A compound according to claim 3 wherein Z is selected from the group consisting of (a) —OCONHR$^4$ wherein R$^4$ is C$_{3-6}$ cycloalkyl;

(b) —N(R$^2$)COR$^3$ wherein R$^2$ is selected from the group consisting of hydrogen and C$_{1-4}$ alkyl and R$^3$ is C$_{3-6}$ cycloalkyl;

(c) —N(R$^2$)SO$_2$R$^3$ wherein R$^2$ is selected from the group consisting of hydrogen and C$_{1-4}$ alkyl and R$^3$ is C$_{3-6}$ cycloalkyl;

(d) —N(R$^2$)CONR$^4$R$^5$ wherein R$^2$ is selected from the group consisting of hydrogen and C$_{1-4}$ alkyl, R$^5$ is selected from the group consisting of C$_{1-4}$ alkyl, and R$^4$ is C$_{3-6}$ cycloalkyl; and (e) —N(R$^2$)COOR$^3$ wherein R$^2$ is selected from the group consisting of hydrogen and C$_{1-4}$ alkyl, and R$^3$ is C$_{3-6}$ cycloalkyl.

5. A compound according to claim 4 wherein Z is N(CH$_3$)SO$_2$R$^3$.

6. A compound according to claim 5 wherein R$^3$ is C$_{3-6}$ cycloalkyl.

7. A compound according to claim 6 wherein R$^3$ is cyclohexyl.

8. A compound according to claim 4 wherein Z is —OCONHR$^4$ wherein —(CHR$^1$)$_m$— is —CH$_2$CH$_2$— and R$^4$ is C$_{3-6}$ cycloalkyl.

9. A compound according to claim 4 wherein —(CHR$^1$)$_m$ is —CH$_2$— or —CH$_2$CH$_2$—; and Z is N(R$^2$)CONR$^4$R$^5$ wherein each of R$^2$ and R$^5$ is hydrogen or C$_{1-4}$ alkyl; and R$^4$ is C$_{3-6}$ cycloalkyl.

10. A compound according to claim 9 wherein Z is N(R$^2$)CONR$^4$R$^5$ wherein each of R$^2$ and R$^5$ is C$_{1-4}$ alkyl and R$^4$ is C$_{5-6}$ cycloalkyl.

11. The compound according to claim 10 wherein each of R$^2$ and R$^5$ is methyl, R$^4$ is cyclohexyl and —(CHR$^1$)$_m$— is —CH$_2$—, said compound being 6,7-dimethoxy-1-[4-(1,3-dimethyl-3-cyclohexylureidomethyl)piperidino]phthalazine.

12. The compound according to claim 10 wherein R$^4$ is cyclopentyl, each of R$^2$ and R$^5$ is methyl, and —(CHR$^1$)$_m$— is —CH$_2$CH$_2$—, said compound being 6,7-dimethoxy-1-[4-(2-[1,3-dimethyl-3-cyclopentylureido]ethyl)piperidino]phthalazine.

13. A pharmaceutical composition useful for stimulating the heart of an animal comprising a compound according to claim 1 and a pharmaceutically acceptable carrier.

14. A method for stimulating the heart of an animal which comprises administering to said animal a heart stimulating amount of a compound according to claim 1.

* * * * *